United States Patent [19]

Bloom et al.

[11] 4,098,276
[45] Jul. 4, 1978

[54] SYRINGE PUMPING HANDLE GRIP AND METHOD OF ASSEMBLING SAME

[75] Inventors: William George Bloom; Howard Fred Newman, both of Los Angeles; Gerald Warren Schmidt, Studio City, all of Calif.

[73] Assignee: American Hospital Supply Corporation, Evanston, Ill.

[21] Appl. No.: 747,417

[22] Filed: Dec. 6, 1976

[51] Int. Cl.² ............................................. A61M 5/00
[52] U.S. Cl. ................................. 128/215; 128/218 C
[58] Field of Search ............... 128/215, 218 R, 218 C, 128/218 F, 220, 221, 234

[56] References Cited

U.S. PATENT DOCUMENTS

| | | | |
|---|---|---|---|
| 2,823,674 | 2/1958 | Yochem | 128/218 C |
| 2,882,901 | 4/1959 | DeVenezia | 128/218 C |
| 3,122,280 | 2/1964 | Goda | 128/218 C |
| 3,863,807 | 2/1975 | Shapiro et al. | 128/218 C X |

Primary Examiner—John D. Yasko

[57] ABSTRACT

A hypodermic syringe with a snap fitted handle grip retained on the syringe by a cam lug. A spring biased plunger of the syringe is attached to a metering rod extending longitudinally along side the plunger and through a guide passage in the handle grip. This metering rod has a circumferentially gripping spring stop that is manually slidable along the metering rod to set a particular dosage for the pumping syringe. A dispensing end of the syringe is connected to a double check valve system which is in turn connected to a reservoir container. This syringe pumping system is useful in hospital pharmacies for filling a series of smaller syringes or vials with metered dosages of diluent of medicament from a larger bulk reservoir container. It is also useful for hospital procedures, such as a thoracentesis, or other industrial or laboratory uses.

13 Claims, 3 Drawing Figures

SYRINGE PUMPING HANDLE GRIP AND METHOD OF ASSEMBLING SAME

BACKGROUND OF THE INVENTION

In hospitals containing many patients, it is common practice to preload hypodermic syringes and other vials in a hospital pharmacy and then store or immediately transfer them to the particular floors for injection into patients.

Many of the medicaments and diluents for modifying concentrations of medicaments are supplied to hospital pharmacies in bulk sterilized containers. The pharmacist transfers measured dosages from these bulk containers to a series of smaller syringes or vials.

Metering syringes to dispense a repeated measured dosage to such smaller containers have been proposed in the past. These have included expensive reusable metal housings with screw thread dosage regulators. These had to be cleaned and sterilized between usages with different sterile medicament and diluents. In addition to their expense, these prior metal housing type metering syringes required laborious screw threading to change the dosage setting. Also, there have been elaborate stop mechanisms to measure dosage that included extensive structure extending behind the thumb pressure area of the syringe. Some included long screw mechanisms coaxial with the syringe barrel. These were cumbersome to handle.

Recently it has been proposed to provide a disposable thermoplastic syringe with a double check valve system for dispensing repeated measured dosages of medicament for diluents. Since a conventional plastic disposable hypodermic syringe was connected to such double check valve system, it had small finger flanges, and also lacked a settable dosage stop mechanism. For each vial or syringe charged with medicament or diluent, the particular dosage had to be visually read from the calibrations of the conventional disposable plastic syringe.

SUMMARY OF THE INVENTION

This invention overcomes the problems with the prior valved dispensing syringe systems for charging a large number of small syringes and vials from a medicament or diluent in a large reservoir container. This invention includes a conventional plastic hypodermic syringe with a special handle grip providing a large gripping area for the pharmacist for firm control. A hypodermic syringe barrel is longitudinally inserted through a passage from a rear of the handle grip and is retained by the handle, either with a syringe biased lug or with a metering rod extending parallel to and along side a plunger of the syringe. In the latter retention system, a spring on the syringe's plunger urges a finger flange of the syringe against the handle grip. This is because the metering rod holds the syringe plunger spring in compression.

The handle grip includes a longitudinal guide passage for the metering rod which is connected to a cap member that fits over a spring biased plunger of the syringe. A stop means on the metering rod sets the particular dosage for the syringe pumping system and abuts a stop surface on the handle grip.

All parts of the pumping system including the conventional syringe, handle grip, and dosage setting mechanism are of inexpensive thermoplastic or wire spring construction so as to be economically discarded along with a double check valve and flexible tube for connecting to a reservoir container after a series of syringes or vials have been filled with a particular medicament or diluent.

The syringe metering system of this invention is very compact for easy manipulation. The system is not substantially longer than the syringe itself.

DETAILED DESCRIPTION

Figure 1:
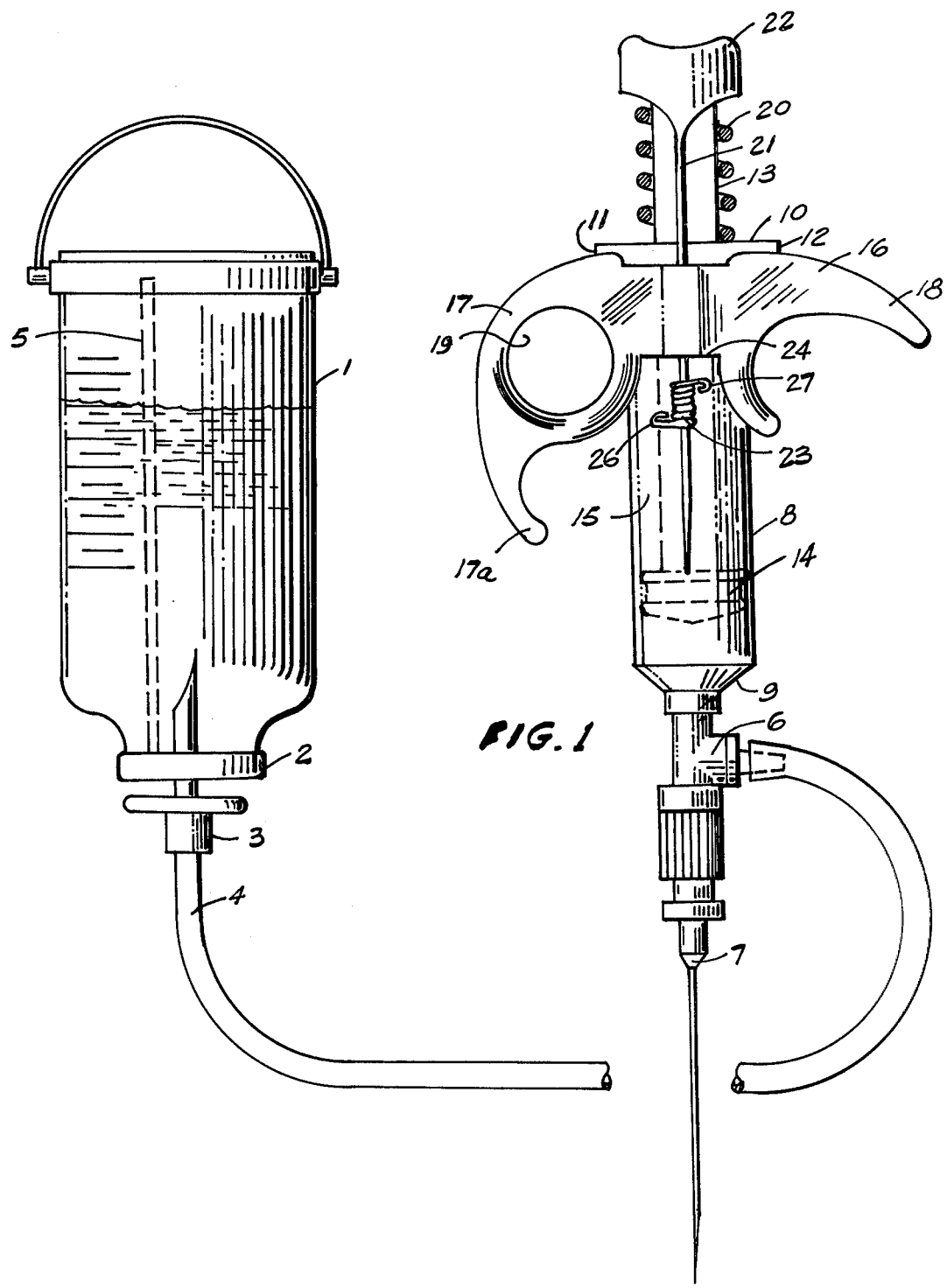
FIG. 1 is a front elevational view of the syringe pumping system.

In FIG. 1 a system is shown for dispensing measured dosages of a medicament or diluent from a reservoir container 1. Container 1 is hung 2-3 feet above a dispensing syringe. Connected to an outlet neck 2 of bottle 1 is a tubular spike 3. As liquid drains through tubular spike 3 to a flexible tube 4, air is replaced in container 1 through air tube 5. If desired, an air inletting spike could be used to replace tubular spike 3. Such an air inletting spike could have two passages, a first liquid outlet passage connected to tube 4 and a second air inlet passage with a check valve and filter. The second passage would permit air entrance into container 1 and prevent liquid seepage through the air inletting spike's second passage.

Liquid from container 1 drains through flexible tube 4 to a double check valve system 6 which is connected to a dispensing needle 7 or other coupling structure for joining to a syringe, vial, or other tubular conduit. The details of the double check valve system are explained in more detail in a copending application, filed 12-06-76, Ser. No. 747,416, invented by Pradip Choksi et al.

Connected to the double check valve 6 is a conventional disposable plastic syringe 8, which has a forward dispensing end 9 and a rear end 10. Adjacent rear end 10 are a pair of finger flanges 11 and 12. A longitudinally movable plunger 13 with a stopper 14 is used to fill and empty a barrel 15 of syringe 8.

For dispensing perhaps several hundred dosages from a single syringe, the small finger flanges 11, 12 of a conventional syringe do not give adequate firm control. Therefore, this invention provides a special handle grip 16 with gripping arms 17 and 18 which extend substantially beyond finger grips 11 and 12 in a lateral direction. Gripping arm 17 is shown with a finger hole 19 for improved control and a hanging hook 17a.

The plunger 13 of the conventional disposable syringe is shown biased in a rearward direction by a compression coil spring 20. This coil spring 20 causes the plunger 13 to retract and automatically draw liquid into the syringe barrel 15 from reservoir container 1. Just how much liquid is drawn into barrel 15 is controlled by a longitudinal metering rod 21 joined to a cap 22 fitting over a rear end of plunger 13. The metering rod 21 and attached cap 22 stops the rearward movement of spring biased plunger 13 when a spring stop member 23 on metering rod 21 abuts a surface 24 on the gripping handle. The spring 20 being under compression urges finger flanges 11 and 12 into abutment with the handle grip. This compression will usually be sufficient to hold the handle grip and syringe together. However, if additional securement is needed, or if the plunger spring is eliminated, then a spring biased cam lug is used.

Figure 2:
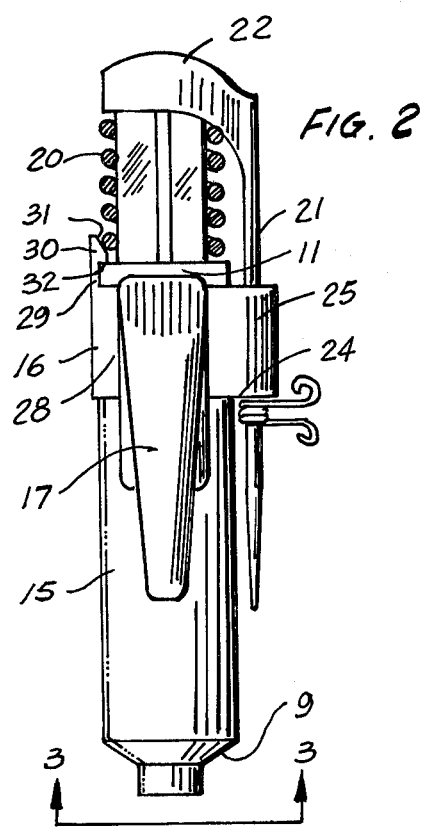
FIG. 2 is an enlarged side elevational view, partially cut away, of the syringe, handle grip, and dosage stop mechanism of the system.

The metering rod 21 is guided in its longitudinal travel through a guide passage 25 in the handle grip. To change the particular dosage setting the spring stop means has a pair of protruding ear portions 26 and 27 extending from ends of a coil spring section. Pinching ears 26 and 27 together causes the coil spring 23 to circumferentially expand so it can be repositioned at a new dosage setting on metering rod 25. The enlarged view of FIG. 2 shows the handle grip 16 with a body member 28, shown here with its grasping arm 17. Body member 28 also includes a longitudinal passage for insertion of syringe barrel 15. Connected to body member 28 is a cam lug structure that includes a thin flexible web section 29 joined to a head section 30 with a beveled lead-in surface 31.

The disposable syringe is assembled to the handle grip by inserting a forward end 9 through a rear entrance of the handle grip's longitudinal passage. The finger grip 11 is urged into contact with the handle grip 16 by plunger spring 20. When a cam lug is used, an edge of the syringe contacts beveled lead-in surface 31 causing rib 29 to temporarily flex outwardly until a shoulder surface 32 of the lug can snap behind a rear surface of the syringe barrel. By manually flexing the cam lug outwardly, the handle grip can be disconnected from the syringe barrel, if desired.

The function of the metering rod, cap 22, handle grip guide passage 25, and spring stop 27 explained in the description of FIG. 1 can be seen from a different view in FIG. 2.

Figure 3:
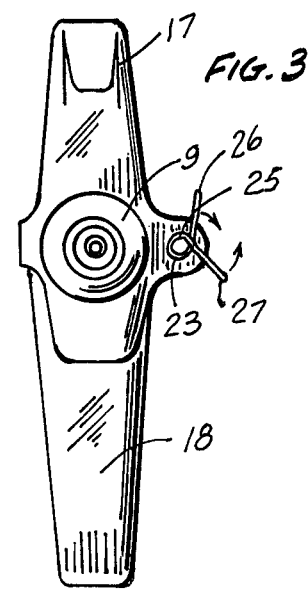
FIG. 3 is a bottom plan view taken along line 3—3 of FIG. 2.

In FIG. 3 the functioning of ears 26 and 27 on the coil spring can best be seen. By squeezing these ears together, the spring slightly uncoils, causing its circumference to slightly increase. This slight increase in its circumference allows longitudinal sliding along measuring rod 21 without the tedious thread screwing of previous setting mechanisms. Release of ears 26 and 27 causes the coil spring to tightly grip metering rod 25 again. If desired, metering rod 25 could be roughened or contain a series of score lines to reduce any chance of spring 23 slipping on metering rod 25.

This invention has been found to work very well when the gripping handle and metering rod with attached cap are formed of Acrylonitrile-butadiene-styrene (ABS) thermoplastic material, however other suitable plastic materials could be used.

In the above description a specific example has been used to describe the invention. However, it is understood that those skilled in the art can make certain modifications to this example without departing from the spirit and scope of the invention.

We claim:

1. A handle grip for a hypodermic syringe that has a barrel with a finger flange, said handle grip comprising: a body member with a longitudinal opening of a size and dimension for axially receiving a syringe; and a snap lock including a flexible spring biased cam lug connected to the body member for securing the body member to a syringe and preventing relative axial movement between the body member and a syringe.

2. A handle grip as set forth in claim 1, wherein the body member and lug form an integral one-piece thermoplastic unit.

3. A handle grip as set forth in claim 1, wherein the cam lug includes a thin flexible web section and a head section with a beveled lead-in surface.

4. A handle grip as set forth in claim 1, wherein the longitudinal opening extends through the body member, with the body member completely encircling the longitudinal opening.

5. A handle grip as set forth in claim 1, wherein the body member has a transverse grasping arm.

6. A handle grip as set forth in claim 1, wherein the securing means is a spring biased metering rod connected with a handle grip and which is axially movable relative to such handle grip; and said metering rod has stop means connected therewith to limit its axial movement relative to the handle grip.

7. A handle grip and hypodermic syringe assembly comprising: a hypodermic syringe with a forward dispensing end, a rear plunger receiving end, a longitudinally slidable plunger having a thumb pressure pad, and a finger flange on a tubular syringe barrel; a handle grip with a longitudinal bore through which the syringe barrel extends; said handle grip and syringe combination having means to secure the syringe and handle against relative axial movement; said assembly having a thermoplastic metering rod extending parallel to and along side the syringe plunger; said metering rod being connected with the plunger; and a threadless lever actuated dose metering stop means on the metering rod which circumferentially grips the thermoplastic metering rod without substantial scarring of such rod as the stop means is banged against the handle grip.

8. A handle grip and hypodermic syringe assembly as set forth in claim 7, wherein the thermoplastic metering rod is integrally joined to a thermoplastic cap fitting over the syringe plunger.

9. A handle grip and hypodermic syringe assembly as set forth in claim 7, wherein the dose adjustment means includes a spring circumferentially gripping said metering rod.

10. A handle grip and hypodermic syringe assembly as set forth in claim 9, wherein the spring includes a pair of levers in the form of squeezable ears to release the spring's circumferential grip on the metering rod for longitudinally sliding to a different dose setting.

11. A handle grip and hypodermic syringe assembly as set forth in claim 7, wherein the syringe barrel has a forward tip connected to a double check valve system, which is in turn connected to a reservoir container through a flexible tube for dispensing repeated measured doses of the reservoir container's contents.

12. A syringe with a barrel, a plunger longitudinally slidable within the barrel, and a dose metering stop means, wherein the improvement comprises: a longitudinal thermoplastic metering rod to control the longitudinal travel of the plunger relative to the barrel; and a threadless lever actuated circumferentially gripping spring stop means on the metering rod, said spring stop means having a lever structure for manually disengaging its grip on the metering rod for longitudinally sliding the stop means to a different dose setting, and to firmly grip the thermoplastic rod at such setting without substantial scarring of the rod.

13. The improvement in a metering rod and spring stop means as set forth in claim 12, wherein the spring stop means includes a coil spring with a lever in the form of an ear section protruding from each end of the coil spring, said ears being offset from each other, whereby manually pinching the protruding ears causes the coil spring to temporarily increase its circumference for sliding along the metering rod.

* * * * *